United States Patent
Crouzet et al.

(10) Patent No.: US 6,884,430 B1
(45) Date of Patent: Apr. 26, 2005

(54) FORMULATION OF STABILIZED CATIONIC TRANSFECTION AGENT(S) /NUCLEIC ACID PARTICLES

(75) Inventors: Joël Crouzet, Sceaux (FR); Bruno Pitard, Sceaux (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/369,883

(22) Filed: Aug. 9, 1999

Related U.S. Application Data

(63) Continuation of application No. PCT/FR98/00222, filed on Feb. 6, 1998.

(30) Foreign Application Priority Data

Feb. 10, 1997 (FR) ............................................. 97 01467

(51) Int. Cl.$^7$ ............................................... A61K 9/127
(52) U.S. Cl. .................... 424/450; 435/320.1; 435/458; 536/23.1; 536/24.5
(58) Field of Search ....................... 424/450; 435/320.1, 435/458; 536/23.1, 24.5

(56) References Cited

U.S. PATENT DOCUMENTS 5,789,244 A * 8/1998 Heidrun et al. .......... 435/320.1
6,086,913 A * 7/2000 Tam et al. ................... 424/450
6,534,484 B1 * 3/2003 Wheeler et al. .............. 514/44

FOREIGN PATENT DOCUMENTS

| WO | WO 96/04932 | 2/1996 |
|---|---|---|
| WO | WO 96/30051 | 10/1996 |
| WO | WO 96/40964 | 12/1996 |
| WO | WO 97/11682 | 4/1997 |

OTHER PUBLICATIONS

Liu et al., New Cationic Lipid Formulations for Gene Transfer, Pharmaceutical Research, vol. 13(12): 1856–60 (1996).

Hara et al., Emulsion formulations as a vector for gene delivery in vitro and in vivo, Advanced Drug Delivery Reviews, vol. 24:265–71 (1997).

* cited by examiner

*Primary Examiner*—James Ketter
(74) *Attorney, Agent, or Firm*—Finnegan, Henderson, Farabow, Garrett, & Dunner, L.L.P.

(57) ABSTRACT

The invention concerns a composition containing stabilized particles of cationic transfection agents/nucleic acid complexes characterized in that it includes besides said transfection agent and nucleic acid at least a non-ionic surfactant in sufficient amount for preventing the aggregation of the particles in course of time. In a preferred embodiment, the surfactant is a polyoxyalkylene or a derivative thereof.

35 Claims, 5 Drawing Sheets

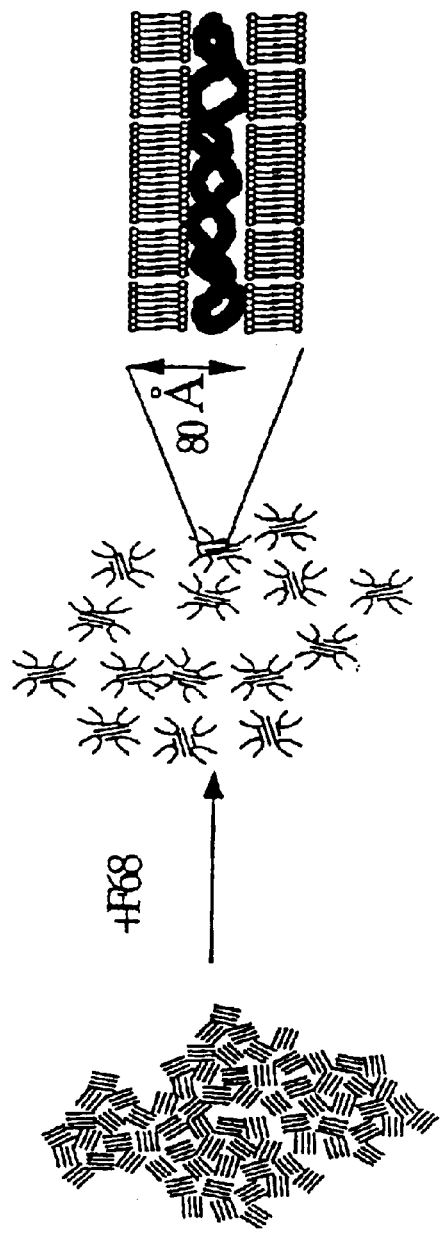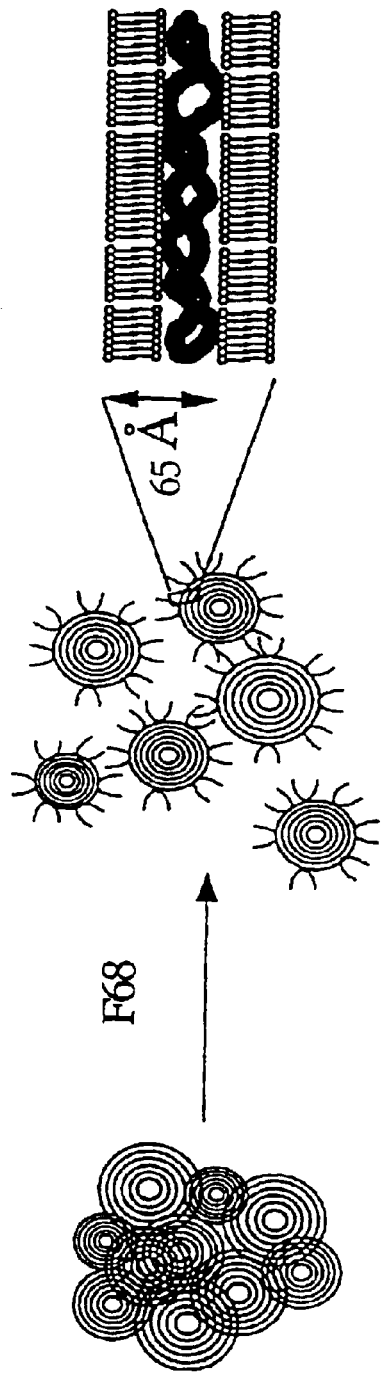
Figure 5A
Figure 5B

FORMULATION OF STABILIZED CATIONIC TRANSFECTION AGENT(S) /NUCLEIC ACID PARTICLES

This application is a continuation of International Application No. PCT/FR98/00222, filed Feb. 6, 1998, the content of which is incorporated herein by referenced.

BACKGROUND OF THE INVENTION

The present invention relates to cationic transfection agent(s)/DNA combinations whose particles are stabilized in size with the aid of a nonionic surface-active agent and to their uses in gene therapy.

Numerous genetic diseases are associated with a defect in expression and/or an abnormal, that is to say a deficient or excessive, expression of one or more nucleic acids. The main objective of gene therapy is to correct this type of genetic abnormality through cellular expression in vivo or in vitro of cloned genes.

Nowadays, several methods are proposed for the intracellular delivery of this type of genetic information. One of them, in particular, is based on the use of chemical or biochemical vectors. Synthetic vectors have two main functions: complexing the DNA to be transfected and promoting its cellular attachment as well as its passage across the plasma membrane and, where appropriate, across the two nuclear membranes. Among the synthetic vectors developed, the cationic polymers of the polylysine and DEAE-dextran type or alternatively lipofectants are the most advantageous.

A major advance was accomplished in this mode of transfection with the development of a technology based on the use of cationic transfection agents of the lipofectant type and more precisely of cationic lipids. It has thus been demonstrated that a positively charged cationic lipid, N-[1-(2,3-dioleyloxy)propyl]-N,N,N-trimethylammonium chloride (DOTMA) interfered, in the form of liposomes or of small vesicles, spontaneously with DNA, which is negatively charged, to form lipid-DNA complexes capable of fusing negatively charged, to form lipid-DNA complexes capable of fusing with the cell membranes, and thus allowed the intracellular delivery of the DNA.

Since DOTMA, other cationic lipids have been developed on this model of structure: lipophilic group combined with an amino group via a "spacer" arm. Among these, there may be mentioned more particularly those comprising, as lipophilic group, two fatty acids or a cholesterol derivative, and comprising, in addition, where appropriate, as amino group, a quaternary ammonium group. DOTAP, DOBT or ChOTB may be mentioned in particular as representatives of this category of cationic lipids. Other compounds, such as DOSC and ChOSC, are characterized by the presence of a choline group in place of the quaternary ammonium group.

Another category of lipofectants, the lipopolyamines, has also been described. In general, it is an amphiphilic molecule comprising at least one hydrophilic polyamine region combined, through a so-called spacer region, with a lipophilic region. The polyamine region of lipopolyamines, which is cationically charged, is capable of reversibly combining with the nucleic acid, which is negatively charged. This interaction greatly compacts the nucleic acid. The lipophilic region makes this ionic interaction insensitive to the external medium by coating the nucleolipid particle formed with a lipid film. In this type of compounds, the cationic group may be represented by the radical L-5-carboxyspermine which contains four ammonium groups, two which are primary and two which are secondary. The compounds DOGS and DPPES belong thereto. These lipopolyamines are most particularly effective for the transfection of primary endocrine cells. As representative of this last family of compounds, there may be mentioned more particularly the lipopolyamines described in particular in Patent Applications WO 96/17823 and WO 97/18185.

However, the efficacy of these synthetic vectors remains to be improved particularly in terms of formation of a complex with nucleic acid and more precisely from the point of view of the stability of the particles of these nucleolipid complexes. Indeed, with conventional nucleic acid/cationic transfection agent formulations, a phenomenon of aggregation of the particles of complexes is frequently and rapidly observed. Such aggregates obviously possess a size which is hardly compatible with a therapeutic transfection. One of the solutions proposed up until now for overcoming this type of precipitation phenomenon consists in introducing into the formulation the cationic transfection agent, such as for example lipofectant, in an excessive quantity, that is to say in a lipofectant/nucleic acid charge ratio of the order of 10 or more. In addition to the fact that such a solution is not always effective, it is not completely satisfactory from the point of view of safety. Cationic transfection agents such as lipofectants and cationic polymers are in themselves compounds which, in large quantities, risk exhibiting a relative toxicity for the cells incorporating them.

It would therefore be particularly advantageous to have from the therapeutic point of view cationic transfection agent/nucleic acid formulations possessing reduced charge ratios and nevertheless stabilized over time in the form of nonaggregated particles. However, as stated above, the nucleic acid/lipofectant concentration zones corresponding to such charge ratios are generally associated with an unstable physical state. A phenomenon of aggregation of the nucleolipid particles is rapidly observed. Furthermore, it is also known that the presence of a salt of the NaCl type, which is conventionally used in cationic transfection agent/nucleic acid formulations, can induce, at certain concentrations, the precipitation of the nucleolipid particles. Thus, the greater the salt concentration, the greater the transfection agent concentration range for which the precipitation is observed.

BRIEF DESCRIPTION OF THE INVENTION

The objective of the present invention is to enhance the value of these cationic transfection agent/nucleic acid concentration zones, which are advantageous from the safety point of view for their reduced quantities of vector and also from the point of view of interference with other proteins given their reduced charge. Indeed, when the complexes have a relatively low charge, the risk of them interfering with serum proteins in vivo is significantly reduced. This is of course particularly advantageous for the transfer of nucleic acids in vivo (Remy, J. S. Proc. Natl. Acad. Sci. USA 1995; 92, 1744–1748). Numerous articles refer to this type of interactions between serum proteins and liposomes (Senior, J. H. et al. Biochim. Biophys. Acta 1991, 1070, 173–179; Hernandez-Caselles, T et al. Molecular and cellular Biochemistry 1993, 120, 119–126; Oku, N. et al. Biochim. Biophys. Acta 1996, 1280, 149–154). Data have also been published on the activation of the complement system by DNA-based complexes used for gene therapy. The degree of activation of complement depends on the cation/DNA ratio (or charge ratio). The latter phenomenon is especially true for polycations such as polylysines, lipospermines (for example DOGS). The activation of complement is less sensitive to the charge ratio for the quaternary ammoniums such as DOTAP, DC-Chol or DOTMA (Plank, C. et al. Human Gene Therapy 1996, 7, 437–1446).

Consequently, it would be particularly advantageous to have from the therapeutic point of view formulations of cationic transfection agent/nucleic acid complexes at a high concentration of nucleic acids and/or at charge ratios which are reduced or even close to neutral and which are, in addition, stabilized in a fluid form of the colloidal type, that is to say which are nonaggregated, two features which are apparently naturally irreconcilable.

Unexpectedly, the applicant has demonstrated that the addition of a nonionic surface-active agent to particles of cationic transfection agent(s)/nucleic acid complexes which are at naturally unstable, that is to say which are capable of progressing rapidly to the formation of aggregates, made it possible to effectively block this phenomenon and therefore to stabilize the particles of complexes at a particle size of less than or of the order of 160 nm.

The first subject of the present invention is a composition useful in gene therapy comprising particles of cationic transfection agent(s)/nucleic acid complexes, characterized in that it incorporates, in addition, at least one nonionic surface-active agent in a sufficient quantity to stabilize the size of the said particles at a size of less than or equal to 160 nm.

For the purposes of the invention, stabilized particles are intended to designate particles whose size is not likely to vary over time when, in particular, these particles are maintained in dispersion in a solution. Unlike the conventional formulations, that is to say free of nonionic surface-active agent, the claimed compositions can be stored for a longer period of time without any modification, of the aggregation type in particular, being noted in this dispersion. The size of the particles thus stabilized generally varies between 50 and 160 nm, preferably between 75 and 150 nm.

In the absence of the claimed nonionic surface-active agent, the particles of complexes present in the claimed composition lead spontaneously to particulate aggregates greater than 160 nm in size.

Moreover, the applicant has demonstrated that the compositions according to the invention possess a lamellar structure having alternatively bilayers of lipids and intercalated layers of DNA.

The nonionic surface-active agents in accordance with the present invention preferably possess at least one hydrophobic segment and at least one hydrophilic segment. The hydrophobic part may equally well be an aliphatic chain, a polyoxyalkylene, an alkylidene polyester, a polyethylene glycol with a dendritic benzyl polyether head, or cholesterol. As for the hydrophilic part, it may be a polyoxyalkylene, a polyvinyl alcohol, a polyvinylpyrrolidone or a saccharide.

Preferably, the surface-active agent used within the framework of the present invention is or comes from a nonionic polyol and more particularly from a polyoxyalkylene with alkylene groups of different lengths and/or conformations or otherwise within the polymer.

More preferably, it corresponds to the following general formula:

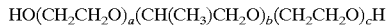

with a, b and c representing, independently of each other, integers which may vary between 20 and 100 inclusive.

The nonionic agent is preferably present in the compositions according to the invention at a concentration of between 0.01% to 10% weight/volume of the said composition and more preferably between 0.02% and 5% weight/volume.

The presence of such a nonionic surface-active agent in combination with the complexes is advantageous for several reasons:

According to the invention, the cationic transfection agent(s) and nucleic acids are present in the composition in a charge ratio which is of course favourable to the development of an aggregation phenomenon. This implies that the positive charges carried by the cationic transfection agent(s) are only in a slight excess compared with the negative charges carried by the complexed nucleic acid, or at best balance them completely. Such a charge ratio is particularly advantageous from the in vivo point of view since it is less damaging in terms of interaction with serum or other proteins such as for example albumin and is more advantageous from the safety point of view. By way of illustration, this charge ratio preferably varies between 1 and 6, and it is more preferably less than 4.

Furthermore, this surface-active agent is completely compatible with in vivo administration. In the case of the formulations according to the invention, it is indeed not necessary to remove this nonionic surface-active agent prior to their injection into the cells to be treated.

Finally, the compositions according to the invention can be advantageously stored. The presence of the nonionic surface-active agent effectively blocks any precipitation phenomenon within the said composition.

By way of preferred surface-active agent according to the invention, there may be mentioned most particularly the compound of general formula:

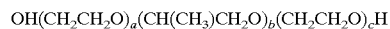

with a equal to 75, b to 30 and c to 75.

Other preferred nonionic surface-active agents are polyethylene glycol with a dendritic benzyl polyether head, polyoxyethylene alcohols or polyoxyethylene nonylphenyl ether.

Cationic transfection agent preferably designates, according to the invention, cationic polymers and lipofectants.

As regards more particularly lipofectants, it is intended to cover for the purposes of the invention under this name any compound or mixture with a lipid character and positively charged, already proposed as active agent with regard to the cellular transfection of nucleic acids.

In general, they are amphiphilic molecules comprising at least one lipophilic region combined or otherwise with a hydrophilic region.

By way of representative of the first family of compounds, there may be proposed in particular lipid mixtures capable of forming cationic liposomes. These formulations may thus contain POPC, phosphatidylserine, phosphatidylcholine, cholesterol, lipofectamine or maleimidophenylbutyrylphosphatidylethanolamine combined with a cationic lipid as defined below.

According to a specific embodiment of the invention, the lipofectant agent used possesses a cationic region.

By way of illustration of this type of cationic lipids constructed on the model of structure: lipophilic group combined with an amino group through a so-called "spacer" arm, there may be mentioned more particularly DOTMA and also those comprising, as lipophilic group, two fatty acids or a cholesterol derivative, and comprising, in addition, where appropriate, as amino group, a quaternary ammonium group. DOTAP, DOBT or ChOTB may be mentioned in particular as representatives of this category of cationic lipids. Other compounds, such as DOSC and ChOSC, are characterized by the presence of a choline group in place of the quaternary ammonium group.

Advantageously, the lipofectants suitable for the invention may also be chosen from lipopolyamines whose polyamine region corresponds to the general formula:

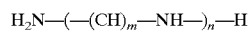

in which m is an integer greater than or equal to 2 and n is an integer greater than or equal to 1, it being possible for m to vary between the different groups of carbon between 2 amines, this polyamine region being covalently combined with a lipophilic region of the saturated or unsaturated hydrocarbon chain of cholesterol type, or a natural or synthetic lipid capable of forming lamellar or hexagonal phases. This polyamine region is more preferably represented by spermine or one of its analogues which has conserved its nucleic acid-binding properties.

Patent Application EP 394 111 describes lipopolyamines of this family which are capable of being used within the framework of the present invention. By way of representative of these lipopolyamines, there may be mentioned more particularly dioctadecylamidoglycyl spermine (DOGS) and the palmitoylphosphatidylethanolamine 5-carboxyspermylamide (DPPES).

The lipopolyamines described in Patent Application WO 96/17823 may also be advantageously used according to the invention. They are represented by the general formula:

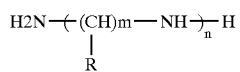

in which R represents

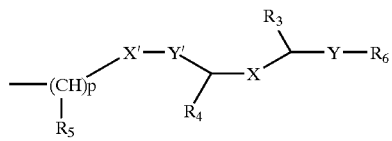

where X and X' represent, independently of each other, an oxygen atom, a methylene group —$(CH_2)_q$— with q equal to 0, 1, 2 or 3, or an amino group —NH— or —NR'—, with R' representing a $C_1$ to $C_4$ alkyl group, Y and Y' represent, independently of each other, a methylene group, a carbonyl group or a group C=S, $R_3$, $R_4$ and $R_5$ represent, independently of each other, a hydrogen atom or a substituted or unsubstituted $C_1$ to $C_4$ alkyl radical, with p capable of varying between 0 and 5, $R_6$ represents a cholesterol derivative or a dialkylamino group —$NR_1R_2$ with $R_1$ and $R_2$ representing, independently of each other, a saturated or unsaturated, linear or branched $C_{12}$ to $C_{22}$ aliphatic radical.

By way of representative of these lipopolyamines, there may be most particularly mentioned 2,5-bis(3-aminopropylamino)pentyl (dioctadecylcarbamoylmethoxy) acetate and 1,3-bis(3-aminopropylamino)-2-propyl (dioctadecylcarbamoyl-methoxy)acetate.

Finally, new lipopolyamines, whose values can also be enhanced within the framework of the present invention, have more recently been described in Patent Application WO 97/18185. They are compounds of general formula as follows:

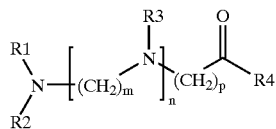

in which $R_1$, $R_2$ and $R_3$ represent, independently of each other, a hydrogen atom or a group —$(CH_2)_q$—NRR' with q being capable of varying between 1, 2, 3, 4, 5 and 6, independently between the different groups $R_1$, $R_2$ and $R_3$ and R and R' representing, independently of each other, a hydrogen atom or a group —$(CH_2)_{q'}$—$NH_2$, q' being capable of varying between 1, 2, 3, 4, 5 and 6, independently between the different groups R and R', m, n and p represent, independently of each other, an integer capable of varying between 0 and 6 with, when n is greater than 1, m being capable of taking different values and $R_3$ different meanings within the general formula and $R_4$ represents a group of general formula:

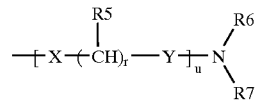

in which $R_6$ and $R_7$ represent, independently of each other, a hydrogen atom or a saturated or unsaturated $C_{10}$ to $C_{22}$ aliphatic radical with at least one of the two groups different from hydrogen, u is an integer chosen between 0 and 10 with, when u is an integer greater than 1, $R_5$, X, Y and r being capable of having different meanings within the different units [X—$(CHR_5)_r$—Y], X represents an oxygen or sulphur atom, or an amine group which is monoalkylated or otherwise, Y represents a carbonyl group or a methylene group, $R_5$ represents a hydrogen atom or a natural amino acid side chain, substituted if appropriate, and r represents an integer varying between 1 and 10 with, when r is equal to 1, $R_5$ representing a substituted or unsubstituted natural amino acid side chain, and when r is greater than 1, $R_5$ representing a hydrogen atom.

By way of representative of these lipopolyamines, there may be more particularly mentioned those which follow: $\{(H_2N(CH_2)_3\}_2N(CH_2)_4N\{(CH_2)_3NH_2\}(CH_2)_3NHCH_2COGlyN[(CH_2)_{17}CH_3]_2H_2N$ $(CH_2)_3NH(CH_2)_4NH$ $(CH_2)_3NHCH_2COGlyN[(CH_2)_{17}CH_3]_2H_2N(CH_2)_3NH$ $(CH_2)_4NH(CH_2)_3NHCH_2COArgN[(CH_2)_{17}CH_3]_2$. In a particularly advantageous manner, it is possible to use, within the framework of the invention, lipofectamine, dioctadecylamidoglycyl spermine (DOGS), palmitoylphosphatidylethanolamine 5-carboxyspermylamide (DPPES), 2,5-bis(3-aminopropylamino)pentyl (dioctadecylcarbamoylmethoxy) acetate, 1,3-bis(3-aminopropylamino)-2-propyl (dioctadecylcarbamoyl-methoxy)acetate, $\{H_2N(CH_2)_3\}_2N$ $(CH_2)_4N\{(CH_2)_3NH_2\}(CH_2)_3NHCH_2COGlyN[(CH_2)_{17}CH_3]_2$, $H_2N(CH_2)_3NH(CH_2)_4NH(CH_2)_3NHCH_2COGlyN[(CH_2)_{17}CH_3]_2$, and/or $H_2N(CH_2)_3NH(CH_2)_4NH(CH_2)_3NHCH_2COArgN[(CH_2)_{17}CH_3]_2$. This may also be cationic lipids incorporating one or more guanidinium and/or amidinium groups, such as more particularly those described by J. M. Lehn et al. (Proc. Natl. Acad. Sci. U.S.A, 1996, 93, 9682–9686).

According to the present invention, the cationic polymer capable of being used as cationic transfection agent is preferably a compound of general formula (I) as follows:

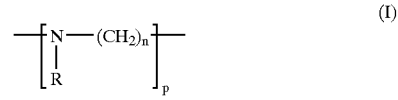

in which R may be a hydrogen atom or a group of formula:

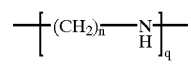

n being an integer between 2 and 10, p and q being integers, it being understood that the sum p+q is such that the average molecular weight of the polymer is between 100 and $10^7$ Da.

It is understood that, in the formula (I) above, the value of n may vary between the different units p. Thus, the formula (I) groups together both homopolymers and heteropolymers.

More preferably, in the formula (I), n is between 2 and 5. In particular, the polymers of polyethylene imine (PEI) and of polypropylene imine (PPI) exhibit completely advantageous properties. The polymers preferred for carrying out the present invention are those whose molecular weight is between $10^3$ and $5 \times 10^6$. By way of example, there may be mentioned the polyethylene imine of average molecular weight 50,000 Da (PEI50K), the polyethylene imine of average molecular weight 22,000 Da (PEI22K) or the polyethylene imine of average molecular weight 800,000 Da (PEI800K).

PEI50K, PEI22K and PEI800K are commercially available. As for the other polymers represented by the general formula (I), they can be prepared according to the process described in Patent Application FR 94/08735.

In the compositions of the present invention, the nucleic acid complexed with the cationic transfection agent may be both a deoxyribonucleic acid and a ribonucleic acid. These may be sequences of natural or artificial origin, and in particular genomic DNA, cDNA, mRNA, tRNA, rRNA, hybrid sequences or synthetic or semisynthetic sequences of oligonucleotides, modified or otherwise. These nucleic acids may be of human, animal, plant, bacterial or viral origin and the like. They may be obtained by any technique known to persons skilled in the art, and in particular by screening libraries, by chemical synthesis or alternatively by mixed methods including chemical or enzymatic modification of sequences obtained by screening libraries. They may be chemically modified.

As regards more particularly the deoxyribonucleic acids, they may be single- or double-stranded, as well as short oligonucleotides or longer sequences. These deoxyribonucleic acids may carry therapeutic genes, sequences for regulating transcription or replication, antisense sequences, modified or otherwise, regions for binding to other cellular components and the like.

For the purposes of the invention, therapeutic gene is understood to mean in particular any gene encoding a protein product having a therapeutic effect. The protein product thus encoded may be a protein, a peptide and the like. This protein product may be homologous with respect to the target cell (that is to say a product which is normally expressed in the target cell when the latter exhibits no pathology). In this case, the expression of a protein makes it possible, for example, to compensate for an insufficient expression in the cell or for the expression of a protein which is inactive or weakly active because of a modification, or alternatively to overexpress the said protein. The therapeutic gene may also encode a mutant of a cellular protein having increased stability, a modified activity and the like. The protein product may also be heterologous with respect to the target cell. In this case, an expressed protein may, for example, supplement or provide an activity which is deficient in the cell, allowing it to combat a pathology, or stimulate an immune response.

Among the therapeutic products for the purposes of the present invention, there may be mentioned more particularly enzymes, blood derivatives, hormones, lymphokines: interleukins, interferons, TNF and the like (FR 92/03120), growth factors, neuro-transmitters or precursors thereof or synthesis enzymes, trophic factors: BDNF, CNTF, NGF, IGF, GMF, aFGF, bFGF, NT3, NT5, HARP/pleiotrophin and the like, dystrophin or a minidystrophin (FR 91/11947), the protein CFTR associated with cystic fibrosis, tumour suppressor genes: p53, Rb, Rap1A, DCC, k-rev and the like (FR 93/04745), the genes encoding factors involved in clotting: factors VII, VIII and IX, the genes involved in DNA repair, suicide genes (thymidine kinase, cytosine deaminase), genes for haemoglobin or other carrier proteins, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as for example lipoprotein lipase, hepatic lipase, lecithin cholesterol acyltransferase, 7-alpha-cholesterol hydroxylase, phosphatidic acid phosphatase, or alternatively proteins for transfer of lipids such as the protein for transfer of cholesterol esters and the protein for transfer of phospholipids, a protein for binding HDLs or alternatively a receptor chosen, for example, from the LDL receptors, receptors for remnant chylomicrons and scavenger receptors, and the like.

The therapeutic nucleic acid may also be a gene or an antisense sequence, whose expression in the target cell makes it possible to control the expression of genes or the transcription of cellular mRNAs. Such sequences may, for example, be transcribed in the target cell into RNAs complementary to cellular mRNAs and thereby block their translation into protein, according to the technique described in Patent EP 140 308. The therapeutic genes also comprise the sequences encoding ribozymes, which are capable of selectively destroying target RNAs (EP 321 201).

As indicated above, the nucleic acid may also comprise one or more genes encoding an antigenic peptide capable of generating an immunoresponse in man or in animals. In this specific embodiment, the invention therefore allows the production either of vaccines or of immunotherapeutic treatments applied to man or to animals, in particular against microorganisms, viruses or cancers. This may be in particular antigenic peptides specific for the Epstein-Barr virus, the HIV virus, the hepatitis B virus (EP 185 573), the pseudorabies virus, the syncytia forming virus or other viruses, or alternatively specific for tumours (EP 259 212).

Preferably, the nucleic acid also comprises sequences allowing the expression of the therapeutic gene and/or of the gene encoding the antigenic peptide in the cell or desired organ. They may be sequences which are naturally responsible for the expression of the gene considered when these sequences are capable of functioning in the infected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to infect. Likewise, they may be promoter sequences derived from the genome of a virus. In this regard, there may be mentioned, for example, the promoters of the E1A, MLP, CMV and RSV genes and the like. In addition, these expression sequences can be modified by the addition of activating or regulatory sequences and the like. The promoter may be inducible or repressible.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the therapeutic product synthesized to a specific compartment of the cell.

In another embodiment, the claimed compositions may comprise, in addition, an adjuvant of the type, comprising dioleoylphosphatidylethanolamine (DOPE), oleoylpalmitoylphosphatidylethanolamine (POPE), di-stearoyl, -palmitoyl, -myristoyl phosphatidylethanolamines as well as their derivatives which are N-methylated 1 to 3 times, phosphatidylglycerols, diacylglycerols, glycosyldiacylglycerols, cerebrosides (such as in particular galactocerebrosides), sphingolipids (such as in particular sphingomyelins) or alternatively asialogangliosides (such as in particular asialoGM1 and GM2).

Very recently, the applicant has demonstrated that it was also particularly advantageous to use, as adjuvant in transfection compositions, a compound involved, directly or otherwise, in the condensation of nucleic acids. This compound consists, completely or in part, of peptide units (KTPKKAKKP) (SEQ ID NO: 1) and/or (ATPAKKAA) (SEQ ID NO: 2), it being possible for the number of units to vary between 2 and 10. Such an agent can also be derived from a portion of a histone, a nucleolin, a protamine and/or one of their derivatives (WO 96/25508). Such a compound may be advantageously incorporated into the claimed composition.

The compositions according to the invention can also use one or more targeting elements which make it possible to direct the nucleic complexes to receptors or ligands at the surface of the cell. By way of example, the composition of the present invention may comprise one or more antibodies directed against molecules of the cellular surface, or alternatively one or more membrane receptor ligands such as insulin, transferrin, folic acid or any other growth factor, cytokines or vitamins. Advantageously, the composition may use lectins, modified or otherwise, so as to target specific polysaccharides at the surface of the cell or on the neighbouring extracellular matrix. Proteins with an RGD unit, peptides containing a tandem array of RGD units, cyclic or otherwise, as well as polylysine peptides can also be used. More recently, there have also been described natural or synthetic ligand peptides which are advantageous in particular for their selectivity with respect to specific cells and which are capable of effectively promoting internalization in these cells (Bary et al. Nature Medicine, 2, 1996, 299–305). These targeting agents are generally conjugated with the cationic transfection agent considered.

The present invention also relates to a process for the preparation of the claimed compositions. More precisely, it relates to a process for the preparation of a composition comprising particles of cationic transfection agent(s)/nucleic acid complexes, stabilized in size, characterized in that the transfecting agent and the nucleic acid are brought into contact in the presence of a sufficient quantity of nonionic surface-active agent to stabilize the particles of nucleic complexes thus formed at a size of less than about 160 nm.

More precisely, one of the components, namely the nucleic acid or the lipofectant, is mixed beforehand with the nonionic surface-active agent before being brought into contact with the second component. The manifestation of any aggregation phenomenon which would have spontaneously manifested itself in the absence of the said nonionic surface-active agent is thus prevented.

The compositions according to the invention may be formulated for administrations by the topical, cutaneous, oral, rectal, vaginal, parenteral, intranasal, intravenous, intramuscular, subcutaneous, intraocular or transdermal route and the like. Preferably, the pharmaceutical compositions of the invention contain a pharmaceutically acceptable vehicle for an injectable formulation, in particular for a direct injection at the level of the desired organ, or for administration by the topical route (on the skin and/or mucous membrane). They may be in particular isotonic, sterile solutions or dry, in particular freeze-dried compositions which, upon addition, depending on the case, of sterilized water or of physiological saline, allow the constitution of injectable solutions. The doses of nucleic acid used for the injection as well as a number of administrations may be adjusted according to various parameters, and in particular according to the mode of administration used, the relevant pathology, the gene to be expressed or the desired duration of treatment. As regards more particularly the mode of administration, it may be either a direct injection into the tissues or the circulatory pathways, or a treatment of cells in culture, followed by their reimplantation in vivo, by injection or transplantation.

The compositions according to the invention are particularly advantageous from the therapeutic point of view. It is henceforth possible to envisage, according to the present invention, effectively administering nucleic acid complexes of appropriate size and of reduced charge ratio, which is particularly beneficial from the in vivo point of view. The serum/nucleic complex interactions generally observed are significantly attenuated with the claimed compositions.

The present invention will be more fully described with the aid of the following examples and figures which should be considered as illustrative and nonlimiting.

BRIEF DESCRIPTION OF THE DRAWINGS

FIG. 5: PART A: Schematic representation of the structure of the RPR 120535/DNA complexes in the absence or in the presence of poloxalkol.

Figure 1:
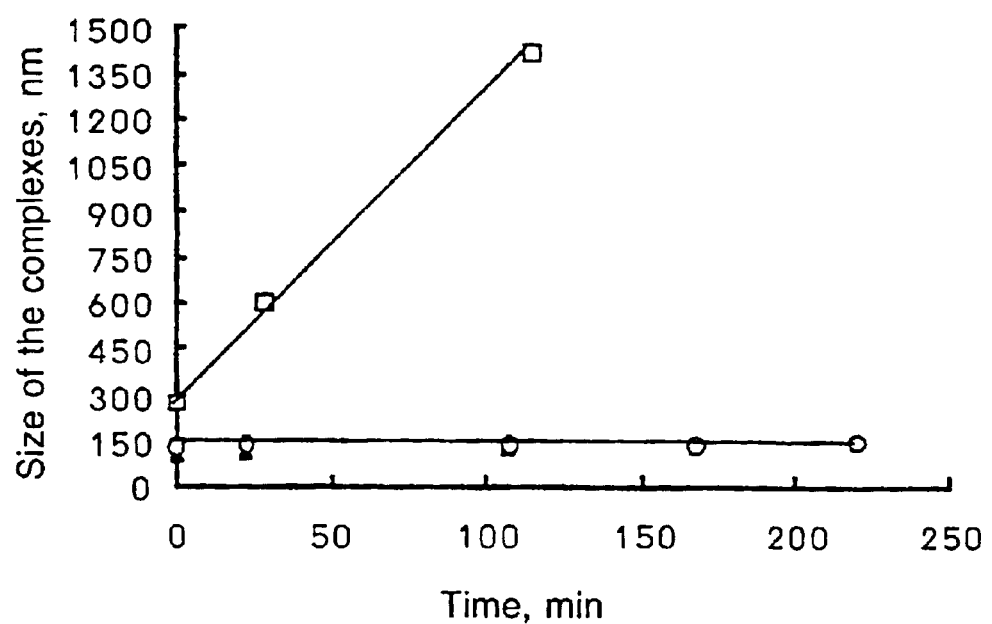
FIG. 1: Effect of poloxalkol on the variation of the size of RPR 120535/DNA complexes, at the charge ratio (+/−) 2.5, as a function of time.

PART B: Schematic representation of the structure of the BGTC/DNA complexes in the absence and in the presence of poloxalkol.

DETAILED DESCRIPTION OF THE INVENTION

Materials

The surface-active agent used in the examples below is the poloxalkol of formula $OH(CH_2CH_2O)_{75}(CH(CH_3)CH_2O)_{30}(CH_2CH_2O)_{75}H$. It is marketed under the trademark Pluronic F68®. The poloxalkol stock solution used in the following examples is 10% (weight/volume) in water.

The DNA used to prepare the samples is the plasmid of pXL2774 described in PCT/FR 96/01414. It is used at a concentration of 0.7 mg/ml in a Tris/EDTA buffer (10 mM/0.1 mM) of pH 7.5.

The cationic lipids used are the following: $H_2N(CH_2)_3NH(CH_2)_4NH(CH_2)_3NHCH_2COGlyN[(CH_2)_{17}CH_3]_2$ (RPR 120535) (acetate salt) and $H_2N(CH_2)_3NH(CH_2)_4NH(CH_2)_3NHCH_2COArgN[(CH_2)_{17}CH_3]$ (RPR 120531) (trifluoroacetic acid salt), both described in PCT/FR 96/01774. They are used at a concentration of 5 mM in water where they are solubilized by heating at 50° C. for 25 minutes, the solutions then being cooled to room temperature.

Methods

The measurement of the hydrodynamic diameter is carried out with a Coulter N4Plus, using plastic cells (four transparent faces) filled with 800 μl of the various solutions, the measurement being carried out at 90° C. in unimodal mode.

The measurements of fluorescence are carried out on Perkin Elmer LS50B, using wavelengths of excitation and emission of 260 nm and 590 nm respectively. The slit widths for excitation and emission are set at 5 nm. The fluorescence value is recorded after adding 5 μg of ethidium bromide/ml final concentration.

The cryo-transmission electron microscopy (cryo-TEM) experiments are carried out with 7 μl of prepared samples containing 0.5 mg of DNA/ml, which are placed on a carbon-coated copper grid covered with a membrane with holes. The grids are then immersed in liquid ethane so as to convert the liquid water to vitrified water. Next, this grid is installed inside a specimen holder cooled with liquid nitrogen and introduced into the microscope (Philips CM12) for visualization.

The low-angle X-ray diffraction experiments are carried out in the synchrotron (LURE) in Orsay (France) on the D43 line. The samples are prepared at 0.5 mg DNA/ml and then centrifuged. The pellets are deposited in a cell in which the two windows consist of kapton. A germanium-containing monochromator (111 reflection) allows the selection of the wavelength of 0.138 nm.

The in vivo transfections are carried out by injecting, into the vein of the tail of 30-day-old mice, 200 μl of a solution containing 0.2 mg DNA/ml combined with a cationic lipid vector. 24 hours after the injection, the mice are humanely killed and then various organs are recovered (lung, liver, heart, kidney, spleen). These organs are then ground in a lysis buffer with the aid of an Ultraturax. The ground products obtained are then centrifuged, and then 10 μl of the supernatant is collected in order to assay the luciferase activity.

EXAMPLE 1
Influence of Poloxalkol on the Size of the RPR 120535/DNA Complexes The plasmid (10 μg/ml) is placed in a solution containing 150 mM NaCl and various concentrations of poloxalkol. The lipofectant RPR 120535 is then added in order to obtain a charge ratio (+/−) 2.5. The size of the complexes is then measured by photon correlation spectroscopy according to the procedure described in Methods. The results are presented in FIG. 1.

It can be noted that in the absence of poloxalkol (□), the particles change from 274 nm to a maximum of 1000 nm in a few tens of minutes. Next, a precipitate is observed after a few hours of incubation.

On the other hand, in the presence of 0.1% (+) poloxalkol, a decrease in the size of the complexes is observed, which size remains stable for a concentration of 0.8% (○) and 1% (▲) poloxalkol and does not vary beyond 150 nm.

The incubation of the lipofectant alone with 1% (weight/volume) poloxalkol does not form particles which are detectable by Quasi-Elastic Diffusion of light. Likewise, when the DNA is incubated with 1% poloxalkol, no particle can be detected.

EXAMPLE 2
Influence of Poloxalkol on the Size of RPR 120531/DNA Complexes

To do this, Example No. 1 was repeated with the cationic lipid RPR 120531.

Figure 2:
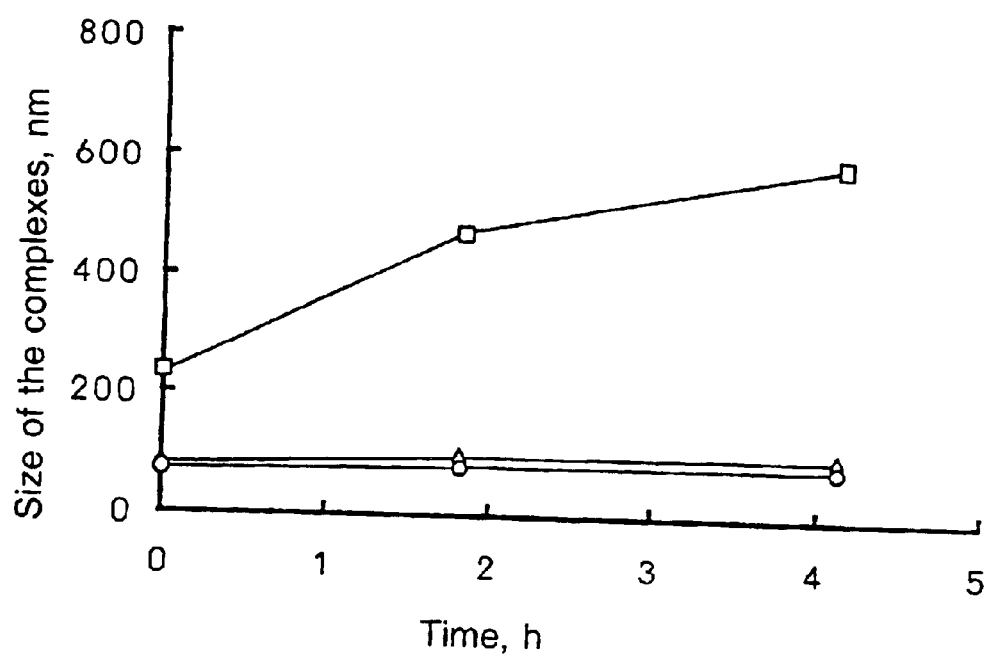
FIG. 2: Effect of poloxalkol on the variation of the size of RPR 120531/DNA complexes, at the charge ratio (+/−) 2.5, as a function of time.

The plasmid (10 μg/ml) is placed in a solution containing 150 mM NaCl at various concentrations of poloxalkol. RPR 120531 is then added in order to obtain a charge ratio (+/−) 2.5. The size of the complexes is measured by photon correlation spectroscopy (Coulter N4plus). The results are presented in FIG. 2.

It is noted that in the absence of poloxalkol, the size of the RPR 120531/DNA complexes varies from 234 nm to 590 nm in a few hours whereas it remains stable in the presence of 0.5% (▲) and 0.9% (○) poloxalkol.

Figure 3:
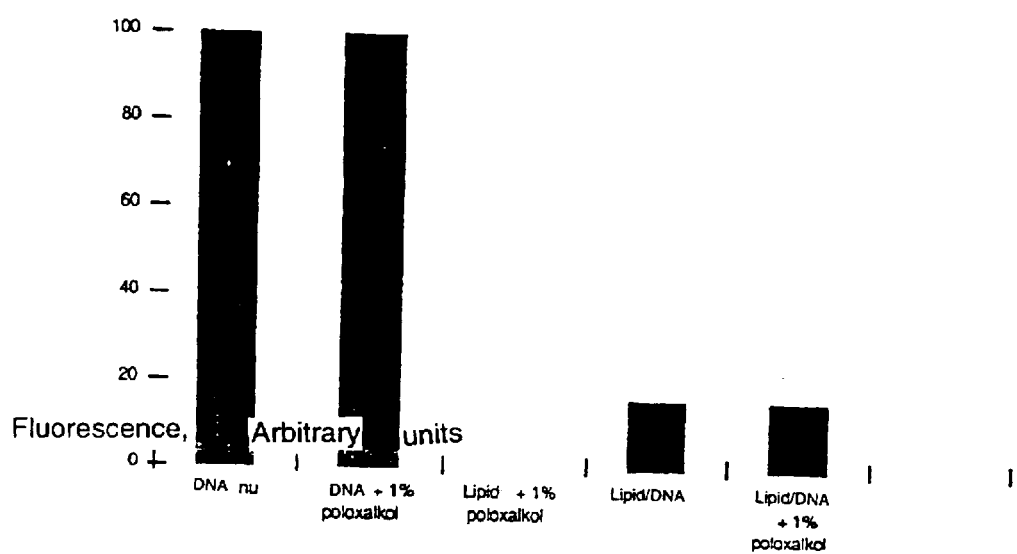
FIG. 3: Effect of poloxalkol on RPR 120535/DNA combinations.

EXAMPLE 3
Control of the Degree of DNA/lipofectant Compaction in the Presence and in the Absence of Poloxalkol It was checked that the particles obtained in the presence of poloxalkol were indeed particles derived from the combination of the DNA with the cationic lipid. For this purpose, experiments for the insertion of a probe, which fluoresces when it is intercalated into the DNA, were carried out. The fluorescence level is high when the DNA is free and, on the other hand, low when it is inaccessible because it is compacted with the cationic lipid. FIG. 3 shows the results obtained.

The fluorescence levels obtained after combination of the DNA with the cationic lipid are observed in the presence and in the absence of poloxalkol. First of all, it can be noted that the fluorescence of the ethidium bromide intercalated into the DNA is not modified by the presence or the absence of 1% poloxalkol. The fluorescence levels of the cationic lipid/DNA complexes (charge ratio (+/−) 2.5) in the presence or in the absence of 1% poloxalkol are indeed of the same order. This residual fluorescence value indicates that the DNA is not accessible for the probe.

In conclusion, poloxalkol does not therefore prevent the combination of the DNA with the cationic lipid to take place normally.

EXAMPLE 4
Transfection in vitro with DNA or RPR 120535 Containing 1% Poloxalkol We wanted to check the effect of poloxalkol when it was mixed with DNA alone or with the cationic lipid alone. For that, the following two samples were prepared:

Sample 1: 10 μg DNA/ml in a medium containing 300 mM NaCl and 1% (weight/volume) poloxalkol.

Sample 2: 60 μM RPR 120535 in a medium containing 300 mM NaCl and 1% poloxalkol.

These samples were prepared by mixing in the order for sample 1: water, NaCl, DNA and poloxalkol, and for sample 2: water, NaCl, poloxalkol and RPR 120535 in the quantities shown in Table I below:

TABLE I

| Test | H$_2$O | NaCl (5M) | DNA (0.7 mg/ml) | Poloxalkol (10%) | RPR 120535 (5 mmol) |
|---|---|---|---|---|---|
| 1 (μl) | 413 | 30 | 7.1 | 50 | 0 |
| 2 (μl) | 414 | 30 | 0 | 50 | 6 |

The biological activity of these two samples is tested on NIH 3T3 cells. A volume of 50 μl of the various samples is deposited per well on a 24-well plate.

The transfection is carried out in the absence of foetal calf serum. The latter is added 2 hours after the addition of the complexes.

The results indicate that no gene transfer is observed with the non-complexed DNA in the presence of 1% poloxalkol and in the absence of 10% foetal calf serum.

Moreover, the assay of total proteins demonstrates that there is no apparent toxicity.

EXAMPLE 5
Transfection in vitro with Solutions of RPR 120535 Lipofectant/DNA Complexes Stabilized at Various Concentrations of Poloxalkol It was sought to assess the effect of the stabilization of the particles with poloxalkol on the transfection efficiency of these particles in the presence of poloxalkol. To do this, samples containing various concentrations of poloxalkol were prepared.

Four samples of charge ratio (+/−) 2.5 are prepared in a medium containing 300 mM NaCl at various concentrations of poloxalkol (0; 0.5%; 0.8% and 1%; weight/volume):

Sample 1: charge ratio (+/−) 2.5, 300 mM NaCl.
Sample 2: charge ratio (+/−) 2.5, 300 mM NaCl, and 0.5% poloxalkol.
Sample 3: charge ratio (+/−) 2.5, 300 mM NaCl, and 0.8% poloxalkol.
Sample 4: charge ratio (+/−) 2.5, 300 mM NaCl, and 1% poloxalkol.

These samples were prepared by mixing in order: water, NaCl, DNA, poloxalkol and RPR 120535, in the quantities shown in Table II below:

TABLE II

| Test | $H_2O$ | NaCl (5M) | DNA (0.7 mg/ml) | Poloxalkol (10%) | RPR 120535 (5 mM) |
|---|---|---|---|---|---|
| 1 (μl) | 737 | 48 | 11.4 | 0 | 4 |
| 2 (μl) | 697 | 48 | 11.4 | 40 | 4 |
| 3 (μl) | 672 | 48 | 11.4 | 64 | 4 |
| 4 (μl) | 657 | 48 | 11.4 | 80 | 4 |

Sample 1 belongs to a cationic lipid concentration range where there is no stability of the particles in solution, that is to say that the particles form aggregates with each other to form large packets of aggregates which possess large hydrodynamic diameters (greater than 1000 nm).

Sample 2 has the same cationic lipid/DNA charge ratio as sample 1, but the mixture is prepared in the presence of 0.5% (weight/volume) poloxalkol. However, this concentration is not sufficient to ensure complete stabilization of the particles (cf. Example No. 1: influence of a nonionic polymer on the size of the RPR 120535/DNA complexes).

Samples 3 and 4 are stable, the hydrodynamic diameter of the particles remain at around 150 nm.

The biological activity of the various formulations is tested on NIH 3T3 cells. A volume of 50 μl of the various samples (containing 10 μg DNA/ml) is added per well. The transfection is carried out in the absence of foetal calf serum. The latter is added 2 hours after adding the complexes. The results obtained are presented in FIG. 4.

Figure 4:
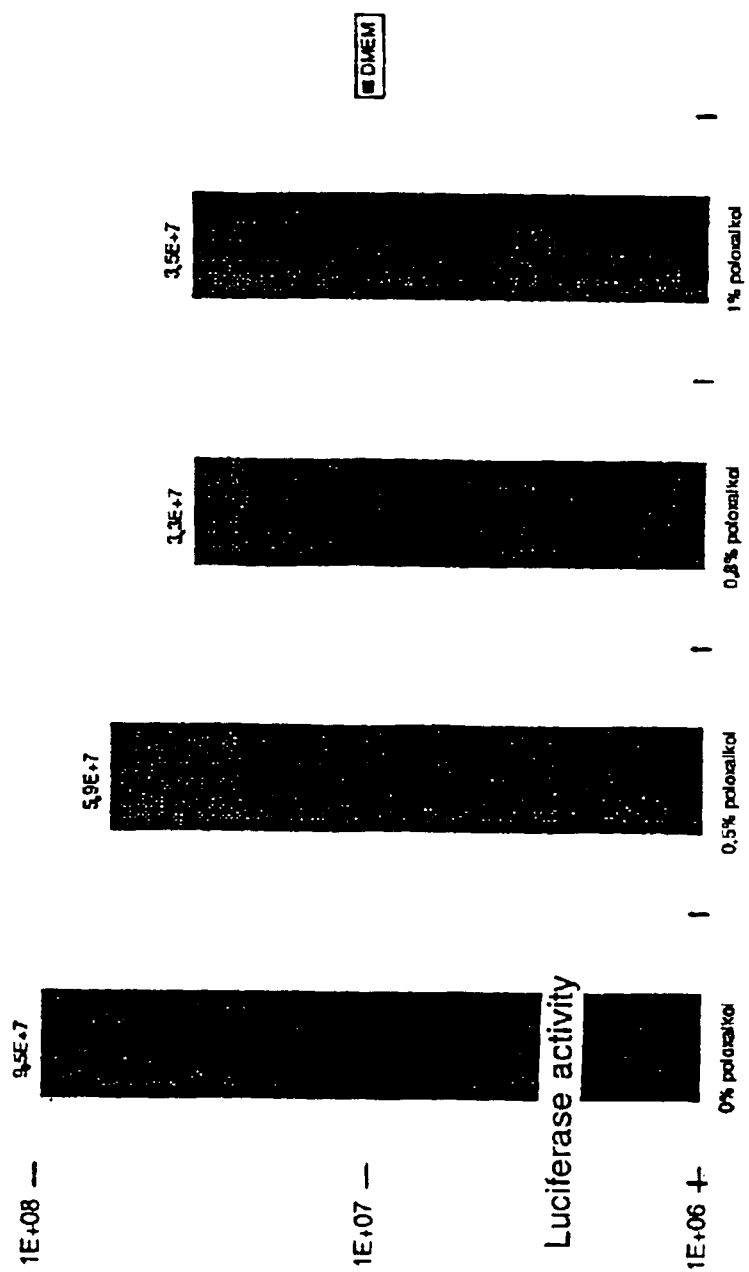
FIG. 4: Effect of poloxalkol on the luciferase activity (RLU/5 µl of lysate) of RPR 120535/DNA complexes, at the charge ratio (+/−) 2.5.

It can be noted in FIG. 4 that poloxalkol, regardless of its concentration, does not alter in vitro transfection in the NIH 3T3 cells. Poloxalkol does not modify the transfection properties, in the absence of foetal calf serum, of the RPR 120535/DNA complexes at the charge ratio (+/−) 2.5.

EXAMPLE 6
Determination of the Structure of the RPR 120535DNA, BGTC/DNA and BGTC/DOPE/DNA Complexes Stabilized with Poloxalkol In this study, we have determined, by low-angle X-ray diffraction and by transmission electron microscopy, the structure of the cationic lipid transfectant/DNA complexes.

FIG. 5A relates to the RPR 120535/DNA complexes. The structure obtained in the absence and in the presence of poloxalkol is a lamellar structure in which the DNA is sandwiched between lipid bilayers whose periodicity is 8 nm. The presence of poloxalkol makes it possible to obtain small-sized complexes, whereas in the absence of poloxalkol, precipitates whose size is greater than 1000 nm are obtained.

FIG. 5B represents the structures obtained with the cationic lipid BGTC (described in Patent Application WO 97/31935). In this case, a lamellar structure whose periodicity is 6.5 nm in the presence or in the absence of poloxalkol is also obtained. The presence of poloxalkol also makes it possible in this case to have small-sized complexes. The results are invariably obtained for complexes containing or otherwise the adjuvant DOPE.

It can therefore be concluded therefrom that the addition of a poloxalkol does not hinder the combination of the DNA with the cationic lipid, but only modifies the colloidal state of this complex.

EXAMPLE 7
Transfection in vivo After Systemic Injection of Cationic Lipid/DNA Complexes Stabilized with Poloxalkol

1) RPR 120535/DNA/F68®

We compared the gene transfer efficiencies after systemic injections of precipitated RPR 120535/DNA complexes, and of these same complexes stabilized by the addition of Pluronic F68®. Table III below indicates that when the complexes are made in the absence of F68®, expression is only observed in the lungs. On the other hand, when the particles are colloidally stabilized by the addition of F68®, the luciferase activity is increased by a factor of 10 in the lungs, and expression is observed in other tissues (liver, heart).

TABLE III

| Lipid | RPR 120535 | |
|---|---|---|
| Formulation | 0% F68 | 10% F68 |
| Mouse | balbc | balbc |
| Lungs | 2 ± 0.9 | 14 ± 0.9 |
| Liver | 0 | 2 ± 3 |
| Kidneys | 0 | 0 |
| Heart | 0 | 1 ± 0.4 |

2) BGTC/DOPE/DNA/F68®

Identical experiments to those described above were carried out using another lipid: BGTC. Similar results were obtained, namely an improvement in gene transfer in the lungs and a measurable expression in the liver, the heart and the kidneys. These results were obtained with various strains of mice (balbc, C57B16, and C57B16 which are deficient in Apolipoprotein E). It is remarkable that identical transfection levels are obtained with C57B16 mice which are normal or deficient in Apolipoprotein E, because they possess a very high lipid level, that is to say ten times more than a normal mouse. Indeed, given that nonviral lipid vectors are used, these complexes might have been expected to be destabilized by the presence of these endogenous lipids in a large quantity. The results of in vivo transfection of BGTC/DOPE/

DNA complexes in the absence or in the presence of poloxalkol are assembled in Table IV below:

TABLE IV

| Lipid | BGTC/DOPE | | | |
|---|---|---|---|---|
| Formulation | 0% F68 | 4% F68 | | |
| Mouse | balbc | balbc | C57B16 | C57B16 KoApoE |
| Lungs | 6.7 ± 2.8 | 86.5 ± 65.4 | 220 ± 99 | 201 ± 12 |
| Liver | 0 | 11.4 ± 11.5 | 47 ± 26 | 47 ± 23 |
| Kidneys | 0 | 0.34 ± 0.16 | 1.8 ± 0.9 | 2.2 ± 0.1 |
| Heart | 0 | 0.74 ± 1.05 | 0.73 ± 0.7 | 0.6 ± 0.0 |

EXAMPLE 8

Use of Other Nonionic Surface-active Agents

Other nonionic surface-active agents were tested: polyethylene glycol dendrimer, polyoxyethylene alcohol, polyoxyethylene nonylphenyl ether. They show the same capacity as F68® to stabilize cationic lipid/DNA complexes. The cationic lipid with which the studies were carried out is RPR 120535.

1) Polyethylene Glycol Dendrimers

We used a dendrimer possessing 1 benzyl polyether head of generation 2 onto which is grafted polyethylene glycol (PEG) of molecular mass 5000 Da (called SAS11), and another dendrimer of the same type, but containing 2 benzyl polyether heads grafted onto a PEG of mass 11,000 Da (called SAS9). Table IV below indicates that with these dendrimers, from 0.02% and above (weight/volume), a micron-size precipitate of transfecting complexes is no longer obtained, but rather particles with a diameter of less than or of the order of 100 nm.

2) Polyoxyethylene Alcohol

This product, also called "Brij", comprising 100 oxyethylene for the hydrophilic part, makes it possible to obtain, after 1 hour, RPR 120535/DNA complexes having a diameter of less than 100 nm.

3) Polyoxyethylene Nonylphenyl Ether

This product also makes it possible to colloidally stabilize the RPR 120535/DNA transfecting complexes. The diameter of the particles is also of the order of 100 nm.

Table V below represents the diameter, in nm, of the RPR 120535/DNA complexes, at the charge ratio of 2.75 (+/−) and containing 0.25 mg of DNA/ml in 150 mM NaCl, stabilized with various nonionic surface-active agents.

TABLE V

| Polymer (w/v) | 0.05% | 0.1% | 0.2% |
|---|---|---|---|
| Brij 700 | 114 nm | 69 nm | 74 nm |
| SAS11 | 152 nm | 99 nm | 71 nm |
| SAS9 | 104 nm | 85 nm | 75 nm |
| Polyoxyethylene nonylphenyl ether | 142 nm | 132 nm | 111 nm |

For all the formulations stabilized with these various nonionic surface-active agents, we checked the state of condensation of the DNA with the cationic lipid by measurements of fluorescence. The results indicated that the presence of these surfactants at the surface of the cationic lipid/DNA complexes does not modify the condensation of the DNA with the cationic lipids (results not shown).

What is claimed is:

1. A composition comprising stabilized particles comprising a complex of at least one cationic transfection agent and a nucleic acid, and at least one nonionic surface-active agent, wherein said agent stabilizes the size of said particles to less than or equal to 160 nanometers;

and wherein the at least one nonionic surface-active agent is chosen from (a) a polyoxyalkylene of the formula:

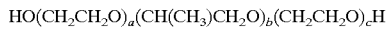

HO(CH$_2$CH$_2$O)$_a$(CH(CH$_3$)CH$_2$O)$_b$(CH$_2$CH$_2$O)$_c$H wherein a, b, and c are, independently, a number from 20 to 100, and (b) a polyethylene glycol comprising a dendritic benzyl polyether head.

2. The composition according to claim 1, wherein the at least one cationic transfection agent and the nucleic acid are present in a charge ratio of between 1 and 6.

3. The composition according to claim 2, wherein the at least one cationic transfection agent and the nucleic acid are present therein in a charge ratio of less than 4.

4. The composition according to claim 1, wherein the at least one non-ionic surface-active agent is a compound of the formula:

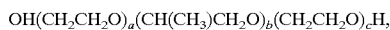

OH(CH$_2$CH$_2$O)$_a$(CH(CH$_3$)CH$_2$O)$_b$(CH$_2$CH$_2$O)$_c$H, wherein a is 75, b is 30, and c is 75.

5. The composition according to claim 1, wherein the at least one non-ionic surface-active agent is present at a concentration ranging from 0.01% to 10% weight/volume of said composition.

6. The composition according to claim 5, wherein the at least one non-ionic surface active agent is present at a concentration ranging from 0.02% to 5% weight/volume of said composition.

7. The composition according to claim 1, wherein the cationic transfection agent is a lipofectant.

8. The composition according to claim 7, wherein the lipofectant is an amphiphilic molecule comprising at least one lipophilic region and a hydrophilic region.

9. The composition according to claim 7, wherein the composition is a lipid mixture comprising cationic liposomes.

10. The composition according to claim 7, wherein the lipofectant is a cationic lipid.

11. The composition according to claim 7, wherein the lipofectant comprises at least one polyamine region of the formula:

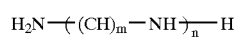

H$_2$N—$(($CH$)_m$—NH$)_n$—H wherein m is a number greater than or equal to 2 and n is a number greater than or equal to 1, wherein when n is greater than 1, m is independently a number greater than or equal to 2, and wherein said polyamine region is covalently bonded to a lipophilic region of a saturated or unsaturated hydrocarbon chain of cholesterol type, or a natural or synthetic lipid capable of forming lamellar or hexagonal phases.

12. The composition according to claim 11, wherein the polyamine region is spermine or an analogue thereof that binds nucleic acid.

13. The composition according to claim 7, wherein the lipofectant is of the formula:

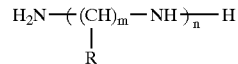

H$_2$N—$(($CH$)_m$—NH$)_n$—H
         |
         R wherein R is a lipophilic region represented by the formula:

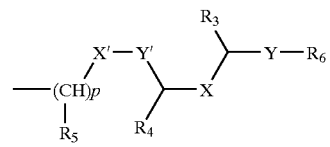

wherein

X and X' are, independently of each other, an oxygen atom, a methylene group —(CH$_2$)$_q$— wherein q is 0, 1, 2 or 3, or an amino group —NH— or —NR' wherein R' is a C$_1$ to C$_4$ alkyl group;

Y and Y' are, independently of each other, a methylene group, a carbonyl group or a group C=S;

R$_3$, R$_4$ and R$_5$ are, independently of each other, a hydrogen atom or a substituted or unsubstituted C$_1$ to C$_4$ alkyl radical;

p is a number from 0 to 5;

R$_6$ is a cholesterol derivative or an alkylamino group —NR$_1$R$_2$ wherein R$_1$ and R$_2$ are, independently of each other, a saturated or unsaturated C$_{12}$ to C$_{22}$ aliphatic radical, wherein said radical is linear or branched.

14. The composition according to claim 7, wherein the lipofectant is a cationic lipid comprising at least one guanidinium or amidinium group or a mixture thereof.

15. The composition according to claim 1, wherein the cationic transfection agent is a cationic polymer.

16. The composition according to claim 15, wherein said cationic polymer is a compound of the formula (I):

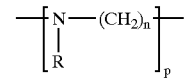

wherein R is a hydrogen atom or a group of formula:

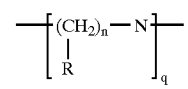

wherein n is a number from 2 to 10, and p and q are numbers wherein the sum p+q is such that the average molecular weight of the polymer ranges from 100 to 10$^7$ Da.

17. The composition according to claim 15, wherein said cationic polymer is a polyethylene imine having an average molecular weight of 50,000 Da (PEI50K), 22,000 Da (PEI22K), or 800,000 Da (PEI800K).

18. The composition according to claim 1, wherein said nucleic acid is a deoxyribonucleic acid.

19. The composition according to claim 1, wherein said nucleic acid is a ribonucleic acid.

20. The composition according to claim 18, wherein the nucleic acid is chemically modified.

21. The composition according to claim 1, wherein said nucleic acid is an antisense nucleic acid.

22. The composition according to claim 1, wherein said nucleic acid comprises a therapeutic gene.

23. The composition according to claim 1, further comprising an adjuvant selected from the group consisting of dioleoylphosphatidylethanolamine (DOPE), oleoylpalmitoylphosphatidylethanolamine (POPE), di-stearoyl, -palmitoyl, and -myristoyl phosphatidylethanolamines optionally substituted with 1 to 3 N-methyl groups, phosphatidylglycerols, diacylglycerols, glycosyldiacylglycerols, cerebrosides, sphingolipids and asialogangliosides.

24. The composition according to claim 1, further comprising a targeting element.

25. The composition according to claim 24, wherein said targeting element is an antibody directed against a cell surface molecule; a membrane receptor ligand selected from the group consisting of insulin, transferrin, folic acid and a growth factor; cytokines; vitamins; lectins; proteins with an RGD unit; peptides containing a tandem array of RGD units wherein said peptides are linear or cyclic; polylysine peptides; natural ligand peptides; and synthetic ligand peptides.

26. A process for making the composition according to claim 1, comprising forming particles by bringing at least one transfecting agent and a nucleic acid into contact in the presence of a sufficient quantity of at least one nonionic surface-active agent to stabilize the particles formed at a size of less than about 160 nm;

and wherein the at least one nonionic surface-active agent is chosen from
(a) a polyoxyalkylene of the formula:

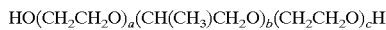

wherein a, b, and c are, independently, a number from 20 to 100, and
(b) a polyethylene glycol comprising a dendritic benzyl polyether head.

27. The process according to claim 26, wherein the nucleic acid or the at least one transfecting agent is mixed before said contact with the at least one nonionic surface-active agent.

28. The composition according to claim 7, wherein the lipofectant is of the formula:

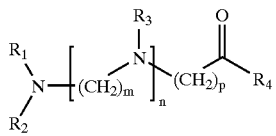

wherein
$R_1$, $R_2$ and $R_3$ are, independently of each other, a hydrogen atom or a group —$(CH_2)_q$—$NRR'$, wherein each q is, independently, 1, 2, 3, 4, 5 or 6, and each R and R' is, independently of each other, a hydrogen atom or a group —$(CH_2)_{q'}$—$NH_2$, wherein q' is independently, 1, 2, 3, 4, 5 or 6;
m, n and p are, independently of each other, a number between 0 and 6, wherein when n is greater than 1, each m is capable of taking different values and each $R_3$ is capable of having different meanings within their respective definitions;

$R_4$ represents a group of formula:

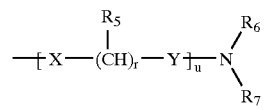

wherein $R_6$ and $R_7$ are, independently of each other, a hydrogen atom or a saturated or unsaturated $C_{10}$ to $C_{22}$ aliphatic radical, with the proviso that $R_6$ and $R_7$ are not both hydrogen atoms;
u is a number from 0 to 10, wherein when u is greater than 1, $R_5$, X, Y and r are capable of having different meanings within the different units;
X is oxygen, sulphur, or an amine group which is monoalkylated;
Y is a carbonyl group or a methylene group;
$R_5$ is hydrogen or a natural amino acid side chain which is optionally substituted; and
r is a number from 1 to 10, wherein when r is equal to 1, $R_5$ is a substituted or unsubstituted natural amino acid side chain, and when r is greater than 1, $R_5$ is hydrogen.

29. The composition according to claim 23, wherein the cerebroside is a galactocerebroside.

30. The composition according to claim 23, wherein the sphingolipid is a sphingomyelin.

31. The composition according to claim 1, wherein said cationic transfection agent is lipofectamine, dioctadecylamidoglycyl spermine (DOGS), palmitoylphosphatidylethanolamine 5-carboxyspermylamide (DPPES), 2,5-bis(3-aminopropylamino)pentyl(dioctadecylcarbamoylmethoxy) acetate or 1,3-bis(3-aminopropylamino)-2-propyl (dioctadecylcarbamoylmethoxy)acetate,

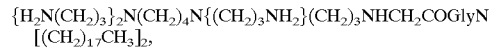

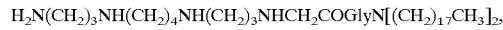

or

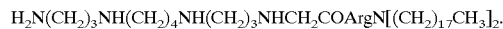

32. The process according to claim 27, wherein the at least one transfecting agent is a lipofectant.

33. The process according to claim 26, wherein the at least one non-ionic surface-active agent is a compound of the formula:

wherein a is 75, b is 30, and c is 75.

34. The process according to claim 26, wherein the at least one non-ionic surface-active agent is present at a concentration ranging from 0.01% to 10% weight/volume of said composition.

35. The process according to claim 34, wherein the surface active agent is present at a concentration ranging from 0.02% to 5% weight/volume of said composition.

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: adjuvant compound, comprising a peptide unit
      having Seq ID 1, for use in transfection compositions; such
      adjuvant compound can be artificially sequenced and/or derived,
      for example, from a portion of a histone, a nucleolin, or a
      protamine

<400> SEQUENCE: 1

Lys Thr Pro Lys Lys Ala Lys Lys Pro
1               5

<210> SEQ ID NO 2
<211> LENGTH: 8
<212> TYPE: PRT
<213> ORGANISM: Artificial Sequence
<220> FEATURE:
<223> OTHER INFORMATION: adjuvant compound, comprising a peptide unit
      having Seq ID 2, for use in transfection compositions; such
      adjuvant compound can be artificially sequenced and/or derived,
      for example, from a portion of a histone, a nucleolin, or a
      protamine

<400> SEQUENCE: 2

Ala Thr Pro Ala Lys Lys Ala Ala
1               5
```